United States Patent [19]

Giegel et al.

[11] Patent Number: 4,517,288
[45] Date of Patent: May 14, 1985

[54] SOLID PHASE SYSTEM FOR LIGAND ASSAY

[75] Inventors: Joseph L. Giegel; Mary M. Brotherton, both of Miami, Fla.

[73] Assignee: American Hospital Supply Corp., Evanston, Ill.

[21] Appl. No.: 227,664

[22] Filed: Jan. 23, 1981

[51] Int. Cl.³ .................. G01N 33/54; C12N 9/96
[52] U.S. Cl. ........................... 435/7; 435/188; 436/514; 436/527; 436/530; 436/538; 436/541
[58] Field of Search .............. 422/55, 56, 57, 58, 422/59, 60, 61; 435/7, 805, 810, 188; 429/1, 8, 12; 23/230 B; 436/524, 527, 528, 529, 530, 532, 538, 541, 514

[56] References Cited

U.S. PATENT DOCUMENTS

| | | | |
|---|---|---|---|
| 2,854,317 | 9/1958 | Free et al. | 23/230 |
| 2,893,843 | 7/1959 | Adams | 23/253 |
| 2,990,253 | 6/1961 | Smelby | 23/253 |
| 3,061,523 | 10/1962 | Free | 195/103.5 |
| 3,645,687 | 2/1972 | Nerenberg | 435/7 |
| 3,791,932 | 2/1974 | Schuurs et al. | 435/7 |
| 3,888,629 | 6/1975 | Bagshawe | 23/230 B |
| 3,951,748 | 4/1976 | Devlin | 195/103.5 R |
| 4,046,514 | 9/1977 | Johnston | 23/253 TP |
| 4,059,405 | 11/1977 | Sodickson et al. | 23/230 R |
| 4,071,315 | 1/1978 | Chauteau | 23/230 B |
| 4,094,647 | 6/1978 | Deutsch et al. | 435/7 |
| 4,157,895 | 9/1979 | Finlay et al. | 23/230 B |
| 4,168,146 | 9/1979 | Grubb et al. | 23/230 B |
| 4,258,001 | 3/1981 | Pierce et al. | 435/7 |
| 4,299,916 | 11/1981 | Litman et al. | 435/7 |
| 4,363,874 | 12/1982 | Greenquist | 435/7 |
| 4,366,241 | 12/1982 | Tom et al. | 435/7 |

OTHER PUBLICATIONS

Giegel et al., "Radial Partition Immunoassay", *Clin. Chem.*, vol. 28, No. 9, (1982), pp. 1894–1898.

*Primary Examiner*—Esther M. Kepplinger
*Attorney, Agent, or Firm*—John H. Faro

[57] ABSTRACT

A method for conducting a ligand assay in an inert porous medium wherein a binding material is immunologically immobilized within the medium, which includes the steps of immunologically immobilizing a binding material within a finite zone of the medium, applying an analyte to the zone containing the immobilized binding material, applying a labeled indicator to the zone which becomes immobilized within the zone in an amount which can be correlated to the amount of analyte in the zone, applying a solvent to substantially the center of the zone to chromatographically separate the unbound labeled indicator from the zone, and measuring the amount of labeled indicator remaining in the zone.

23 Claims, No Drawings

SOLID PHASE SYSTEM FOR LIGAND ASSAY

BACKGROUND OF THE INVENTION

1. Field of Invention

The present invention relates to a solid phase system for ligand assay. More particularly, the invention relates to an immunological method for analyzing biological fluids wherein analytical reactions are conducted in an inert porous medium.

2. Discussion of Prior Art

Variations of natural immunological reactions have been found very useful as analytical techniques. These reactions have been most useful in clinical laboratory procedures, but their use is not limited to clinical applications. Because of the specificity of the reactions, they are of particular advantage in analyzing complex biological fluids. Often, conventional chemical analyses are not capable of differentiating complex molecules in a biological fluid. Such fluids can be analyzed for a variety of components such as drugs, enzymes, hormones, etc. by contacting the fluid with an appropriate antibody. Likewise, analyses for specific antibodies can be conducted by contacting the fluid with an appropriate antigen. Other natural binding proteins are also quite useful in some types of assay procedures.

Unfortunately, the antibody-antigen reaction is generally not directly measurable, therefore, techniques have been devised for its indirect measurement. For instance, an antibody, antigen, or binding protein (collectively referred to as a ligand) may be labeled by various means. The amount of bound labeled ligand can thus be correlated to the concentration of the analyte in the biological fluid. Conventional labels include radioactive tags, e.g., $^{125}I$ or tritium, enzymes, chromophores, fluorophores and enzymes cofactors and effectors. In the case of radioactive tags, the concentration of the labeled ligand is usually determined by placing the compound in a scintillation counter. Enzymes may be measured by reacting the labeled ligand with a substrate, which by the action of the enzyme, releases a chromogenic or fluorogenic substance that can be measured by conventional techniques. Ligands labeled with enzyme cofactors or effectors can be detected similarly by their effect on enzyme action on a substrate. Compounds labeled with chromophores may be directly measurable, e.g., by fluorescence, ultraviolet spectroscopy or other spectroscopic means.

Immunochemical assays generally fall into one of two classifications. In the competitive assay, a limited quantity of binding material is contacted with a solution containing the analyte and a known concentration of a labeled analyte. The labeled and unlabeled analyte compounds compete for the binding sites on the binding material. By reference to a calibration curve, the amount of labeled analyte bound to the binding material can be correlated with the concentration of the analyte in the test solution. A second type of immunological assay, the sandwich assay, involves contacting a binding material with a solution containing the analyte to cause the analyte to bind to the binding material. This complex is then contacted with a solution of a labeled binding material, generally an antibody, which reacts with the bound analyte. The amount of bound labeled binding material is thus directly proportional to the amount of bound analyte.

In all of the described methods, an essential step is to separate the unbound labeled material from the bound labeled material. A technique widely employed for such separation is to immobilize one of the reactants. For instance, an antibody may be adsorbed onto a solid support such as a test tube wall. After labeled material and analyte become bound to the immobilized antibody, the solid support is rinsed free of unbound labeled material. A variety of solid supports have been proposed for this purpose. Such supports include test tube walls, plastic cups, beads, plastic balls and cylinders, paper, and glass fibers.

In U.S. Pat. No. 3,888,629, June 10, 1975, K. D. Bagshawe discloses a reaction cell and an immunoanalytical method, in which antibody is immobilized in a matrix pad of absorbent material such as a glass fiber pad. The reference discloses an antibody impregnated sheet of the absorbent material. Disks or pads of the material are then punched from the mat and placed in a reaction cell. Solutions of the analyte and other reactants are placed on the pad where the immunological reaction occurs. A buffer is then filtered through the pad to wash out unreacted labeled material. Because of surface tension and capillary action, liquid does not easily pass through the pad; therefore, an absorbent material is placed under the pad to facilitate filtration.

To quantitate the reaction conducted in the Bagshawe cell, the pad must be removed from the cell and either placed in a gamma counter (in the case of a radioimmunoassay) or placed in some type of indicator solution (in the case of an enzymeimmunoassay).

A need exists for a rapid, quantitative solid phase ligand assay, which can be conducted entirely on a solid matrix. Advantageously, the method would not require special reaction cells, and the separation of unreacted labeled material could be effected cleanly without filtering large amounts of solvents through the matrix. The amount of binding material deposited in the reaction zone on the solid matrix should be accurately controllable. Such accurate control has not heretofore been realized in prior art methods.

SUMMARY OF THE INVENTION

In accordance with the present invention, a method is disclosed for conducting a ligand assay in an inert porous medium wherein a binding material is immobilized within said medium, the improvement which comprises:

(a) immobilizing a binding material within a finite zone of said medium;

(b) applying to said zone under binding conditions an analyte to which said binding material is specific;

(c) applying to said zone a labeled indicator under conditions which allow said labeled indicator to become immobilized within said zone in an amount which can be correlated to the amount of analyte in said zone;

(d) applying to substantially the center of said zone a stream of solvent in a quantity sufficient to effect a radial chromatographic separation of unbound labeled indicator from said zone; and (e) determining the amount of labeled indicator remaining in said zone.

DETAILED DESCRIPTION OF THE INVENTION

The method of the present invention is conducted in a porous solid matrix. Such matrix is in sheet form and may be made of any suitable inert material which does not deleteriously react with any of the reactants, the products, or the solvents. The term, inert, when referring to the matrix, means that the matrix does not chemically react with any of the materials applied thereto, does not dissolve, does not react immunologically with such materials, and has negligible nonspecific attraction for such materials. Thus, the matrix, or more precisely, the interstices within the matrix, simply acts as a vessel or site for reactions to occur.

The interstices or pores within the matrix are small enough so that the reaction fluid is retained within the matrix by capillary action. The matrix is advantageously a mat of compressed fibers, such as a mat of glass or synthetic fibers or a porous paper mat. The matrix may, however, be constructed of other porous materials such as sintered glass, ceramics, synthetic spongy materials, etc. A glass fiber mat is the preferred matrix because of its inertness. Other materials such as paper tend to have a greater non-specific attraction for the materials applied thereto and may require pretreatment to inactivate reactive sites.

The present invention is useful for a wide variety of biological assays. For instance, blood or urine may be quickly and accurately analyzed for therapeutic drugs, natural or synthetic steroids, hormones, antibodies and the like. Therapeutic drugs which may be determined by this method include digoxin, dilatin, phenobarbital, theophylline, gentamycin, guinidine, propranolol, and the like. Steroids, such as cortisol, aldosterone, testosterone, progesterone and estriol may also be monitored conveniently by the present method. The method may be useful for determining serum or urine levels of hormones such as the thyroid hormones, triiodo-thyronine; the peptide hormones, insulin, coricotropin, gastrin, angiotensin, and proangiotensin; the polypeptide hormones, thyrotropin, luteotropin, and somatotropin, and the like. The binding materials for such assays are generally antibodies specific for the analyte of interest. Such antibodies may be prepared by conventional methods, well known by those skilled in the art. Typically, antibodies are prepared by innoculating an animal, such as rabbit, goat, horse, donkey, sheep, chicken, or human with the antigen of interest, and harvesting the antibodies from the blood of the animal. In addition to antibodies, the binding material may be a non-antibody binding protein, such as vitamin B-12 intrinsic factor, thyroxine binding globulin, folate binding protein, or sex hormone binding protein.

A first step of the present method is to immobilize a binding material within a finite zone of the matrix. Immobilization can be accomplished by any convenient method, such as adsorption, evaporative deposition from a volatile solvent solution, covalent bonding between the binding material and the matrix, or immunological immobilization. Covalent bonding may, for example, involve bonding the binding material to a matrix through a coupling agent, such as cyanogen bromide or glutaraldehyde, as described by Grubb, et al., U.S. Pat. No. 4,186,146 (Sept. 18, 1979). Immunological immobilization is preferred for the practice of the present invention. To immunologically immobilize the binding material within the matrix, the binding material can be reacted with an antibody to such material in a solution absorbed in the reaction zone. In practice, the immunological immobilization may be accomplished by applying to a point on the matrix a small volume, e.g., 2–100 $\mu$l, of a mixture of a solution of the binding material and an antiserum or a solution thereof containing an antibody to the binding material. By capillary action, the mixture diffuses out from the point of application to encompass a finite zone of the matrix. The matrix is then incubated under conditions of temperature and humidity for a period of time sufficient to effect an immunological reaction between the reactants. The reaction conditions will vary depending upon the reactants being used, but generally a temperature of from about $-10°$ C. to about 60° C., preferably from about 0° to about 25° C. is employed, and an incubation time of from about 1 minute to about 24 hours, preferably from about 3 minutes to about 18 hours has been found sufficient to effect the reaction.

For quantitative applications of the present method, the amount of binding material immobilized within the reaction zone should be accurately controlled. One of the advantages of the present method over those described in the prior art is that very accurate control can be achieved through the use of accurate volumetric micropipettes and solutions of known concentrations. The antiserum is generally employed in an amount to insure that substantially all of the binding material is immobilized.

Alternative methods of immobilizing the binding material in the matrix include applying solutions of binding material and antibody to the reaction zone, either sequentially or simultaneously, and incubating to effect the immunological reaction. The matrix sheet may also be impregnated with the antibody by applying a solution thereof uniformly to the sheet and then drying the sheet. As the solution of binding material is spotted on the matrix, the antibody in the reaction zone is redissolved and reacts immunologically with the binding material.

Those skilled in the art will appreciate that a sheet of matrix may have one reaction zone or several. The sheet may be dried after immobilization of the binding material, and stored for prolonged periods before being utilized in an assay procedure. Sheets having multiple reaction zones may have several spots of the same binding material or may comprise different binding materials, for different assays.

Solutions of analyte and labeled indicator are applied to the reaction zone containing the immobilized binding material; and after incubation under appropriate conditions, the immunological reaction occurs resulting in analyte and labeled indicator being bound in the reaction zone. Whether the analyte is applied prior to, concurrently with, or subsequent to the application of the labeled indicator depends upon the type of assay being conducted. For instance, in a competitive assay for an antigen, such as the drug digoxin, the binding material is an anti-digoxin antibody. The analyte, which may be a patient serum, and the labeled indicator, which is suitably labeled digoxin, are applied to the reaction zone substantially concurrently. In a sandwich assay, e.g., for IgG, the labeled indicator would be a labeled anti-IgG antibody, and could be applied to the reaction zone before, after or simultaneously with the reaction between the analyte and the binding material.

The concentrations of analyte and labeled indicator are controlled so that the amounts of such compounds deposited in the reaction zone are appropriate for the particular type of reaction being employed. Such concentrations can be determined in accordance with relationships known in the art. For instance, in a competitive assay, the total amount of analyte and labeled indicator applied to the reaction zone is substantially equal to or greater than that required to bind to all of the binding sites on the binding material. The total concentration of binding sites of the analyte and labeled indicator generally constitute from about 0.1 to about 10, preferably from about 0.5 to about 1.5 times the concentration of binding sites on the binding material. In a sandwich assay, the concentration of the analyte will be such that it can be substantially completely bound in the reaction zone. To accomplish substantially complete binding, generally there is an excess of binding material in the reaction zone with respect to the analyte. The binding material is advantageously employed at a concentration of from about 1 to about 100, preferably about 1 to 10, times that required to bind all of the binding sites of the analyte. The labeled indicator should then be employed in a quantity sufficient to react with the bound analyte. Thus, the labeled indicator is employed in an amount from about 1 to 2, preferably 1 to 1.5, times the amount required to react with all of the bound analyte.

The analyte and labeled indicator are applied to the reaction zone in solution in such a manner that they diffuse throughout substantially the entire reaction zone. Such application is advantageously accomplished by pipetting small volumes of solutions to substantially the center of the zone.

If desired, matrix sheets can be prepared for routine use which have binding material and labeled indicator already applied thereto. The binding material may be applied as described above. The labeled indicator may then be applied to the surface of the matrix, e.g., by a printing process. Advantageously, a barrier layer is applied to the surface prior to application of the labeled indicator to prevent premature reaction of the labeled indicator with the binding material. The barrier layer is a thin coating of a material which is water soluble. Thus, when the analyte is applied to the reaction zone, the barrier layer dissolves and allows the labeled indicator to diffuse into the reaction zone.

The matrix sheet is incubated under conditions which enable the analyte and/or the labeled indicator to be bound to the binding material. A principal advantage of the present invention is that such reactions typically occur very rapidly at room temperature. Generally, incubation temperatures of from about 5° C. to about 60° C. are employed with a preferred temperature in the range of from about 15° to about 40° C. The immunological reactions are usually sufficiently complete in from about a few seconds to about 30 hours, depending on the particular reaction being conducted.

After the reactions have occurred, the unbound labeled indicator is separated from the reaction zone. In accordance with the present invention, the unbound labeled indicator is quickly and quantitatively separated from the reaction zone by a chromatographic procedure. A stream of a solvent, in which the labeled indicator is soluble, is applied to substantially the center of the reaction zone. The solvent may be water or a buffer solution in which such compounds are conveniently dissolved. As the solvent migrates radially out from the center of the reaction zone, unbound reactants are chromatographically separated from the bound reactants. A small quantity of such solvent effectively separates the unbound reactants from the reaction zone. Such reactants, if visible, would appear as a ring around the reaction zone, and the degree of separation is dependent on the volume of solvent zone, and the degree of separation is dependent on the volume of solvent used and the $R_f$ values for the reactants. Small volumes have been found effective for good separation, thus providing a quick, economical, and reliable assay procedure. Typically, solvent volumes of from about 10 $\mu$l to about 150 $\mu$l, preferably 25 to 100 $\mu$l are employed. The solvents may conveniently be applied to the reaction zone with a pipette or hypodermic syringe.

When the present method is being utilized as an enzyme-immunoassay, a solution containing an enzyme substrate may be used for the dual function of applying the substrate and as a chromatographic solvent. Such a procedure reduces the total number of steps and thus reduces the time required to conduct an assay.

After the ligand assay reaction has been completed and the unbound labeled indicator has been separated from the reaction zone, the reaction zone is observed, either visually or with the aid of appropriate instruments, to determine the magnitude of the signal generated by the labeled indicator. This signal might be a measure of radioactivity in the case of a radioimmunoassay, or a colorimetric, ultraviolet or fluorescence response in the case of an enzyme-immunoassay. Typically, colorimetric, ultraviolet, or fluorescent assays may be used for rate determinations, where the rate of formation (or disappearance) of the measured chromophore or fluorophore is compared to a calibration standard as as indication of concentration. Such measurements may be made directly from the porous medium, employing front surface fluorometers or reflectometers. In its simplest form, the present method may be used as a qualitative or semiquantitative test, wherein the reaction zone is observed visually, under visible or ultraviolet light, to determine whether a reaction has occurred or to obtain an approximate indication of the extent of the reaction.

The present invention is further illustrated by the following examples, which are not intended to be limiting.

EXAMPLE I

This example describes a competitive type of enzymeimmunoassay for serum digoxin in accordance with the present invention.

I. REAGENTS

A. Preparation of Anti-Digoxin Papers.

1. Diluent Buffer—$1 \times 10^{-2}$M Phosphate, $1.5 \times 10^{-1}$M NaCl, $1 \times 10^{-2}$M EDTA, pH 7.3, with 0.5% bovine serum albumin and 0.1% $NaN_3$.

2. First antibody-Solution—16 microliters of a 1:100 dilution of rabbit anti-digoxin plus 10 microliters of normal rabbit serum was diluted to a final volume of 2000 microliters.

3. Second antibody solution—1:100 dilution of goat anti-rabbit serum.

4. Paper Matrix—Whatman type GF/F glass microfiber filter paper.

To 175 microliters of first antibody solution was added 175 microliters of second antibody solution. The solution was mixed rapidly and immediately pipetted in 50 microliter aliquots onto the paper matrix. The anti-digoxin papers were incubated in a moist condition at 4° C. for 18 hours. They were then washed with 100 microliters of $1.5 \times 10^{-1}$M NaCl containing 0.1% Triton X-100 which was applied to the center of the antibody spot diffusing out radially. Papers were dried under vacuum and stored at 4° C.

B. Preparation of Enzyme Labeled Digoxin.

1. Digoxin—100 milligrams in 10 milliliters of methanol.

2. Periodate—214 milligrams of sodium periodate in 10 milliliters of 100 millimolar potassium phosphate pH 8.0.

3. Alkaline Phosphatase (ALP)—from *E. coli* dialized against 100 mM Tris buffer pH 8.

4. Sodium Cyanoborohydride—6 milligrams per milliliter in 500 millimolar phosphate pH 6.0.

To 500 microliters of digoxin in methanol was added 500 microliters of periodate suspension. The materials were reacted with agitation for 1 hour in the dark at room temperature. The mixture was centrifuged to remove the periodate. The pH of the supernate was adjusted to 8 with potassium carbonate. The reaction was effective to oxidize the vicinal hydroxyls of the digitose, cleaving the ring and forming the dialdehyde. To the oxidized digoxin was added 200 microliters containing 2 milligrams of alkaline phosphatase. The mixture was incubated in the dark at room temperature for 1 hour. Octanol (1 drop) was added to retard foaming and the pH was adjusted to about 6 with formic acid. The reaction produces Schiff base bonds between the amine groups of the enzyme and the aldehyde groups of the digoxin. The excess aldehydes and the Schiff bases are then reduced by the dropwise addition of 300 microliters of sodium cyanoborohydride. The conjugate thus formed was purified by dialysis (3 times) against saline and by gel filitration chromatography on a Sephadex G-25 column using 10 millimolar Tris, $1.5 \times 10^{-1}$ molar NaCl, pH 8.0 as eluant.

C. Preparation of Calibrator-Trace Mixtures

1. The enzyme labeled digoxin was added to commercial normal human serum calibrators, containing azide preservatives, to form calibration-tracer mixtures having a free digoxin concentration of 0 to 6 nanograms per millimeter and a tracer digoxin concentration of 1.6 nanograms per milliliter.

D. Preparation of Substrate Wash Solution

1. A 10 milligram amount of 4-methylumbelliferyl phosphate was added to 100 milliliters of 1.5 molar Tris, 1 millimolar magnesium chloride, pH 8.0.

II. ASSAY OF DIGOXIN

Three anti-digoxin paper spots were labeled for each calibrator-tracer mixture and each sample-tracer mixture. An aliquot of 50 microliters of the appropriate calibrator-tracer mixture or sample-tracer mixture was pipetted onto the center of the anti-digoxin paper spot. The mixture was quickly absorbed into the matrix. The reaction spot was incubated in a moist chamber at room temperature for 5 minutes. An aliquot of 100 microliters of substrate wash solution was applied slowly (60 seconds) to the center of the spot. The wash solution diffused out radially carrying with it any digoxin-ALP not bound by the anti-digoxin immobilized within the matrix. When the diffusion of the substrate begins to slow, the reaction rate of the antibody bound digoxin-ALP is measured in an area about the center of the antibody spot within a radius of 4.5 millimeters.

A delimited area (4.5 millimeter radius) is chosen for the monitoring of the bound enzyme substrate reaction so as to sample a homogenous area of the anti-digoxin reaction matrix (total radius of 6 millimeters). At the same time the free digoxin-ALP has been removed from the monitored area by the subtrate wash solution (13 millimeter radius).

The enzymatic conversion of the non-fluorescent substrate, 4-methylumbelliferyl phosphate, to the fluorescent product, 4-methylumbelliferone, by the bound digoxin-ALP is measured in a suitable front surface fluorometer.

EXAMPLE 2

This example describes a competitive type of radioimmunoassay for serum digoxin in accordance with the present invention.

I. REAGENTS

A. Preparation of Anti-Digoxin Papers

1. Diluent Buffer—$1 \times 10^{-2}$M phosphate, $1.5 \times 10^{-1}$M NaCl, $1 \times 10^{-2}$M Na$_2$ EDTA, pH 7.3, with 0.5% bovine serum albumin and 0.1% NaN$_3$.

2. Paper Matrix—Toyo type GA-100 glass microfiber filter paper.

To 0.67 milliliters of buffer was added 100 microliters of normal rabbit serum, 20 microliters of 2% patent blue dye and 20 microliters of a 1:100 dilution of anti-digoxin serum. The solution was mixed thoroughly. To this was added 200 microliters of goat anti-rabbit serum. The solution was mixed rapidly and immediately pipetted in 100 microliter aliquots onto the paper matrix. The anti-digoxin papers were incubated in a moist condition at 4° C. for 18 hours. They were then washed with 2 aliquots of 200 microliters each of 100 mM PO$_4$-saline which was applied to the center of the antibody spot, diffusing out radially. Papers were dried under vacuum and stored at 4° C.

B. Preparation of $^{125}$I Labeled Digoxin.

A commercially available $^{125}$I-digoxin derivative was diluted to 915 picograms per milliliter in $1 \times 10^{-2}$M phosphate, $1.5 \times 10^{-1}$M NaCl, $1 \times 10^{-2}$M EDTA, pH 7.3, with 0.5% bovine serum albumin and 0.1% NaN$_3$.

C. Preparation of Calibrator-Tracer Mixtures

The $^{125}$I-digoxin solution was added to commercial normal human serum calibrators containing azide preservative, to form calibration-tracer mixtures having a free digoxin concentration of 0 to 6 nanograms per milliliter and a tracer digoxin concentration of 458 picograms per milliliter.

D. Wash Solution.

$1 \times 10^{-2}$M phosphate, $1.5 \times 10^{-1}$M NaCl.

II. ASSAY OF DIGOXIN.

Anti-digoxin paper spots were labeled for each calibrator-tracer mixture. An aliquot of 100 microliters of the appropriate calibrator-tracer mixture was pipetted onto the center of the anti-digoxin paper spot. The mixture was quickly absorbed into the matrix. The reaction spot was incubated in open air, on a wire rack at room temperature for 3 minutes. Two aliquots of 200 microliters each of wash solution was applied to the center of the spot. The wash solution diffused out radially carrying with any $^{125}$I-digoxin not bound by the anti-digoxin immobilized within the matrix. A disc (radius 9 millimeters) was then punched from the center of the anti-digoxin paper spot. The discs were counted in a gamma scintillation counter for 1 minute each. The number of counts for each disc was found to be inversely proportional to the concentration of digoxin applied to the disc.

EXAMPLE 3

This example describes a sandwich type of radioimmunoassay for serum thyroid stimulating hormone (TSH) in accordance with the present invention.

I. REAGENTS

A. Preparation of anti-TSH papers

1. Diluent Buffer—50 millimolar phosphate, pH 7.4, with 0.1% bovine serum albumin and 0.02% azide.

2. Filter Paper Matrix—Toyo glass fiber paper type GA-100.

To 2.25 milliliters of buffer was added 2.5 milliliters of a 1:100 dilution of goat anti-TSH serum and 250 microliters of rabbit anti-goat serum. The solution was mixed rapidly and immediately pipetted 100 microliter aliquots onto the paper matrix. The spots were incubated in a moist condition at 4° C. for 18 hours. They were then washed 2 times with 200 microliter aliquots of 100 millimolar phosphate buffer pH 7.3. The papers were dried under vacuum and stored at 4° C.

B. $^{125}$I-Anti-TSH Tracer.

A commercial preparation of $^{125}$I labeled rabbit anti-TSH serum containing 58,000 counts per minute per 100 microliters.

C. TSH Calibrators

A commercial secondary standard material was diluted in charcoal treated normal human serum to concentrations of 0, 1.5, 6, 12, 25 and 50 microunits per milliliter.

D. Pre-Application of Tracer to Paper.

To each anti-TSH spot was added 100 microliters of rabbit $^{125}$I-anti-TSH. The spots were dried under vacuum.

II. ASSAY OF TSH.

One anti-TSH paper spot was labeled for each TSH calibrator. 100 microliters of the appropriate calibrator was applied onto the spot. The papers were incubated in a moist chamber for 1 hour at 37° C. Papers were then washed with 2 aliquots of 200 microliters each of 10 mM phosphate pH 7.4. A disc of 9 mm was cut from the center of each spot. All discs were counted in a gamma counter for 1 minute. The number of counts for each disc was found to be proportional to the concentration of TSH applied to the disc.

EXAMPLE 4

This example describes a sandwich type of enzyme immunoassay for human IgG in accordance with the present invention.

I. REAGENTS

A. Preparation of Anti-Human IgG Papers

1. Diluent Buffer—0.01M Tris with 0.1% BSA and 0.5% sodium azide, pH 8.0.

2. First Antibody Solution—2 microliters of goat anti-human IgG is diluted to a final volume of 2000 microliters.

3. Second Antibody Solution—1:100 dilution of rabbit anti-goat serum.

4. Paper Matrix—Whatman type GF/F glass microfiber filter paper.

To 175 microliters of first antibody solution is added 175 microliters of second antibody solution. The solution is mixed rapidly and is immediately pipetted in 50 microliter aliquots onto the paper matrix. The anti-human IgG papers are incubated in a moist condition at 4° C. for 18 hours. Papers are stored at 4° C.

B. Preparation of enzyme labeled anti-human IgG—a modification of the method described by A. Murayamd et al. Immuno-chemistry 15: 523 (1978).

1. Anti-human IgG—20 ml of rabbit anti-human IgG serum is mixed for 4 hours at room temperature with 0.4 gms of Aerosil 380. The material is centrifuged and the supernate collected. The treated rabbit anti-human IgG serum is then diluted with equal volume of 0.1M ethylene diamine (EDA) buffer pH 7.0 and applied to a column of QAE Sephadex which has been equilibrated with the EDA buffer. The column is eluted with additional EDA buffer. The protein fractions which are eluted are pooled and concentrated to 20 mg/ml in an Amicon cell fitted with a type PM10 membrane. The material is then dialyzed against 0.01M K H$_2$PO$_4$.

2. Periodate—32.5 milligrams of sodium periodate are combined with 177.5 milligrams of KCl and 3.0 ml of methanol.

3. Alkaline Phosphatase (ALP)—from *E. coli*. The enzyme is dialyzed against 0.01M phosphate buffer, pH 6.5.

4. Sodium Cyanoborohydride—6 milligrams per milliliter in 0.5M phosphate pH 6.0.

To a test tube wrapped in foil containing 45 $\mu$l of purified rabbit anti-human IgG is added 80 $\mu$l of periodate suspension. The pH is adjusted to between 4.0 and 4.5 with 1N HCl. The mixture is incubated at room temperature with constant mixing for 30 minutes. The mixture is centrifuged and the supernate collected. 20 $\mu$l packed volume of G-25 Sephadex equilibrated with 0.01M K H$_2$PO$_4$ is added to the supernate. The Sephadex is mixed by inverting for 20 minutes at room temperature. The Sephadex is then centrifuged down and the supernate is collected. 16 mg of ALP is added to the supernate and the pH is adjusted to 6.5 with 0.5M K H$_2$PO$_4$. The solution is mixed and then dialyzed against 0.01M phosphate buffer pH 6.5 for 18 hours at room temperature. To the dialyzed conjugate is added 50 $\mu$l sodium cyanoborohydride. The mixture is allowed to react at room temperature for 1 hour. The solution is then dialyzed against 0.01M Tris 0.15M NaCl pH 8.0.

The conjugate is applied to a Biogel A 1.5 column and the fractions containing both enzyme and antibody activities are collected.

C. Preparation of human IgG calibrators. Human IgG is weighed out and dissolved in 0.01M Tris with 1.0% gelatin and 0.1% sodium azide, pH 8.0 to form calibrators having human IgG concentrations of between 0 mg/ml and 50 mg/ml.

D. Preparation of Substrate Wash Solution. A 10 milligram amount of 4-methylumbelliferyl phosphate is added to 100 milliliters of 1.5M Tris, 0.001M MgCl$_2$, pH 8.0.

II. ASSAY OF HUMAN IgG.

Two anti-human IgG paper spots are labeled for each calibrator and each sample. Calibrators and samples are diluted 1:50 in 0.01M Tris, 0.15M NaCl pH 8.0.

The diluted calibrators and samples are pipetted in 50 microliter aliquots onto the center of the anti-human IgG paper spot. The mixture is quickly absorbed into the matrix. The reaction spot is incubated in a moist chamber at room temperature for 5 minutes and the human IgG in the sample is bound by the antibody immobilized within the matrix. An aliquot of 50 microliters of ALP-anti-human IgG conjugate is applied and is incubated at room temperature for 5 minutes. The conjugate binds to the human IgG bound within the matrix. An aliquot of 100 microliters of substrate wash solution is applied slowly to the center of the spot. The wash solution diffuses out radially carrying with it any ALP-anti-human IgG conjugate not bound within the matrix. When the diffusion of the substrate begins to slow, the reaction rate of the bound ALP-anti-human IgG is measured in a suitable fluorometer.

We claim:

1. A competitive method for conducting a solid phase enzyme immunoassay of a fluid sample within the interstices of a solid, inert porous medium, said fluid sample containing an unknown level of analyte, the method comprising a. immobilizing a binding material within a finite zone of the interstices of the solid, inert porous medium, said binding material being capable of immunological reaction with said analyte from among the constituents of the fluid sample;

b. applying, under binding conditions, to substantially the center of said finite zone, containing said immobilized binding material, a fluid sample containing the analyte for which said binding material is specific, said analyte being applied as a solution so as to permit diffusion thereof within the interstices of a reaction zone of the porous medium;

c. applying an enzyme-labeled indicator to substantially the center of said reaction zone, under conditions which allow said indicator and said analyte to compete for binding sites on said immobilized binding material, said indicator, which comprises an enzyme conjugated to a ligand, being immunochemically bound to said immobilized binding material in a amount which can be correlated to the amount of analyte in said reaction zone;

d. applying, to substantially the center of said reaction zone a stream of eluting solvent containing a substrate for the enzyme of said enzyme-labeled indicator, the quantity of said eluting solvent being sufficient to effect radial chromatographic separation, within said porous medium, of unbound enzyme-labeled indicator from bound enzyme-labeled indicator within said reaction zone; and e. observing the extent to which the bound enzyme-labeled indicator is present within a delimited area of said reaction zone by measurement of the level of chromophore or fluorophore produced by the action of the bound enzyme-labeled indicator on said substrate, said delimited area of said reaction zone being essentially free of unbound indicator.

2. The enzyme immunoassay of claim 1, wherein the binding material is immunologically immobilized within a finite zone of the inert, porous medium.

3. The enzyme immunoassay of claim 1, wherein the binding material is an antibody specific for said analyte and is immunologically immobilized within said zone by applying a solution of said antibody to said zone and applying an antiserum to said antibody to said zone, thus effecting an immunological reaction in said zone.

4. The enzyme immunoassay of claim 1, wherein the assay is a competitive enzyme immunoassay for digoxin in a biological fluid; the binding material is digoxin antibody; the labeled indicator is digoxin labeled with alkaline phosphatase enzyme; the eluting solvent is a buffered solution of 4-methylumbelliferyl phosphate, which acts as a substrate for the alkaline phosphatase enzyme and releases 4-methylumbelliferone upon enzyme hydrolysis; and the amount of 4-methylumbelliferone so released is determined by front surface fluorometry.

5. The enzyme immunoassay of claim 1, wherein the analyte is a therapeutic drug and the binding material is an antibody specific for said therapeutic drug.

6. The enzyme immunoassay of claim 5, wherein said therapeutic drug is selected from the group consisting of dilatin, phenobarbital, theophylline, gentamycin, quinidine, and propranolol and said antibody is derived from an animal selected from the group consisting of rabbit, goat, horse, donkey, sheep, chicken and human.

7. The enzyme immunoassay of claim 1, wherein the analyte is a steroid and the binding material is an antibody specific for said steroid.

8. The enzyme immunoassay of claim 7, wherein said steroid is selected from the group consisting of cortisol, aldosterone, testosterone, progesterone and estriol.

9. The enzyme immunoassay of claim 1, wherein the analyte is a thyroid hormone and the binding material is an antibody specific for said thyroid hormone.

10. The enzyme immunoassay of claim 9, wherein said thyroid hormone is triiodothyronine or thyroxine.

11. The enzyme immunoassay of claim 1, wherein the analyte is a peptide hormone and the binding material is an antibody specific for said peptide hormone.

12. The enzyme immunoassay of claim 11, wherein said peptide hormone is selected from the group consisting of insulin, corticotropin, gastrin, angiotensin and proangiotensin.

13. The enzyme immunoassay of claim 1, wherein the analyte is a polypeptide hormone and the binding material is an antibody specific for said polypeptide hormone.

14. The enzyme immunoassay of claim 13, wherein said polypeptide hormone is selected from the group consisting of thyrotropin, luteotropin and somatotropin.

15. The enzyme immunoassay of claim 1, wherein the binding material is a specific binding protein selected from the group consisting of vitamin B-12 intrinsic factor, thyroxine binding globulin, folate binding protein and sex hormone binding protein.

16. In an analytical method for conducting a solid phase enzyme immunoassay of a fluid sample by immunological differentiation of complex molecules in such fluid by first contacting such fluid, containing an unknown level of analyte, and an enzyme-labeled indicator with an immobilized binding material within a reaction zone of a porous medium under conditions favoring immunochemical interaction of said binding material with the analyte and the enzyme-labeled indicator, whereby the analyte of interest of said fluid and the enzyme-labeled indicator compete for available sites on said binding material, said enzyme-labeled indicator comprising an enzyme conjugated to a ligand, applying a wash fluid to said porous medium to remove unreacted enzyme-labeled indicator from said medium, and measuring the amount of enzyme-labeled indicator immunochemically bound to the binding material within the porous medium, the improvement comprising:

a. applying, to substantially the center of a reaction zone within an inert porous medium, a stream of eluting solvent containing a substrate for the enzyme of the enzyme-labeled indicator, the quantity of such eluting solvent applied to said reaction zone being sufficient to effect radial separation, within said inert porous medium, of unbound enzyme-labeled indicator from bound enzyme-labeled indicator within said reaction zone; and b. observing the extent to which the bound enzyme-labeled indicator is present within a delimited area of said reaction zone by measurement of the level of chromophore or fluorophore produced by the action of the bound enzyme-labeled indicator on said substrate, said delimited area of said reaction zone being essentially free of unbound indicator.

17. A sandwich method for conducting an enzyme immunoassay of a fluid sample within the interstices of a solid, inert porous medium, said fluid sample containing an unknown level of analyte, the method comprising:

a. immobilizing a binding material within a finite zone of a solid, inert porous medium, said binding material being capable of immunological reaction with said analyte from among the constituents of the fluid sample;

b. applying, under binding conditions, to substantially the center of said finite zone containing said immobilized binding materials, a fluid sample containing the analyte for which the said binding material is specific, said analyte being applied as a solution so as to permit diffusion thereof within a reaction zone of the solid, porous medium containing the immobilized binding material, whereby substantially all of said analyte is bound to the binding material;

c. applying an enzyme-labeled indicator to substantially the center of said reaction zone, under conditions which allow said labeled indicator to become immunochemically bound to said analyte in a manner which can be correlated to the amount of analyte in the reaction zone, said indicator comprising an enzyme conjugated to a ligand;

d. applying, to substantially the center of said reaction zone, a stream of eluting solvent containing a substrate for the enzyme of said enzyme labeled indicator, said solvent being applied in a quantity sufficient to effect radial separation, within said porous medium, of unbound enzyme-labeled indicator from the indicator which is bound within said reaction zone; and e. observing the extent to which the bound enzyme-labeled indicator is present within a delimited area of said reaction zone by measurement of the level of chromophore or fluorophore produced by the action of the bound enzyme-labeled indicator on said substrate, said delimited area of said reaction zone being essentially free of unbound indicator.

18. Th enzyme immunoassay of claim 17, wherein the binding material is immunologically immobilized within the porous medium.

19. The enzyme immunoassay of claim 17, wherein the analyte is immunoglobulin G, the binding material is an anti-human immunoglobulin G and the enzyme-labeled indicator comprises an enzyme conjugated to anti-human immunoglobulin G.

20. The enzyme immunoassay of claim 19, wherein the enzyme-labeled indicator is anti-human immunoglobin G and the label is an enzyme selected from the group consisting of *E. coli* alkaline phosphatase, betagalactosidase and horse radish peroxidase.

21. The enzyme immunoassay of claim 19, wherein the enzyme-labeled indicator is anti-human immunoglobulin G and the label is a fluorophore selected from the group consisting of fluorescein, rhodamine and fluorescamine.

22. The enzyme immunoassay of claim 19, wherein the analyte is hepatitis suface antigen ($HB_sAg$), the binding material is anti-$HB_sAg$, and the enzyme-labeled indicator is enzyme-labeled anti-$HB_sAg$.

23. In an analytical method for a solid phase enzyme immunoassay of a fluid sample by immunological differentiation of complex molecules in such fluid by first contacting such fluid, containing an unknown level of analyte, with an immobilized binding material within a reaction zone of a porous medium under conditions favoring immunochemical interaction of said binding material with the analyte, whereby substantially all of the analyte of interest of said fluid is immunochemically bound to the binding material, contacting the analyte with an enzyme-labeled indicator under conditions favoring immunochemical interaction of said indicator with the analyte, said indicator comprising an enzyme conjugated to a ligand, applying a wash fluid to said porous medium to remove unreacted enzyme-labeled indicator from said medium and measuring the amount of enzyme-labeled indicator which is immunochemically bound to the analyte, the improvement comprising:

a. applying, to substantially the center of a reaction zone within an inert, porous medium, a stream of eluting solvent containing a substrate for the enzyme of said enzyme-labeled indicator, the quantity of solvent applied to said reaction zone being sufficient to effect radial separation within said porous medium, of unbound enzyme-labeled indicator from bound enzyme-labeled indicator within said reaction zone; and b. observing the extent to which the bound enzyme-labeled indicator is present within a delimited area of said reaction zone by measurement of the level of chromophore or fluorophore produced by the action of the bound enzyme-labeled indicator on said substrate, said delimited area of said reaction zone being essentially free of unbound labeled indicator.

* * * * *